United States Patent
Duich

[19]

[11] Patent Number: 5,947,907
[45] Date of Patent: Sep. 7, 1999

[54] FAILSAFE METHOD AND APPARATUS FOR A MODULAR MULTI-PARAMETER PATIENT MONITOR

[75] Inventor: Michael B. Duich, Dunedin, Fla.

[73] Assignee: Critikon Company, LLC, Tampa, Fla.

[21] Appl. No.: 09/034,686

[22] Filed: Mar. 4, 1998

[51] Int. Cl.⁶ .................................................. A61B 5/0205
[52] U.S. Cl. .......................................................... 600/483
[58] Field of Search ................................... 600/481, 482, 600/483, 484, 485, 508, 522, 523, 509

[56] References Cited

U.S. PATENT DOCUMENTS

| | | | |
|---|---|---|---|
| 5,375,604 | 12/1994 | Kelly et al. | 600/483 |
| 5,590,648 | 1/1997 | Mitchell et al. | 600/483 |
| 5,682,902 | 11/1997 | Herleikson | 600/521 |

*Primary Examiner*—Scott M. Getzow
*Attorney, Agent, or Firm*—Woodcock Washburn Kurtz Mackiewicz & Norris, LLP

[57] ABSTRACT

A failsafe supervisor system for a processing module of a modular multi-parameter patient monitor which detects a module error or malfunction, places such module in a safe state, and alerts the operator to improper operation of the patient monitor module processor hardware or software. Upon detection of a hardware or software error, an inconsistent system/module time-base check, or other malfunctions during module operation, the impaired parameter module and its associated parameter data gathering apparatuses are powered down and the patient monitor system electrically isolates the impaired module in a failsafe manner to a safe state while permitting other parameter modules to continue with their normal operation. The failsafe supervisor system preferably includes a watchdog timer and discrete logic incorporated with the parameter module's microprocessor control system.

17 Claims, 6 Drawing Sheets

FAILSAFE METHOD AND APPARATUS FOR A MODULAR MULTI-PARAMETER PATIENT MONITOR

BACKGROUND OF THE INVENTION

1. Field of the Invention

The present invention relates to a failsafe method and apparatus for a multi-parameter patient monitor with removable processing modules, and more particularly, to a failsafe method and apparatus for separately regulating the operation of each module of the multi-parameter monitor by placing an impaired module in a safe state when errors or module malfunctions are detected, without powering down the entire multi-parameter patient monitor.

2. Brief Description of the Prior Art

Various protection systems have been used in patient monitors in the prior art to detect malfunctions and prevent patient injury. Since protection systems are typically connected with particular functions, such as the turning on and turning off of the patient monitor, they tend to power down the entire patient monitor when an error is detected. A failsafe method and apparatus is desired that operates to power down and electrically isolate a single processing module of a multi-parameter patient monitor rather than to power down the entire monitor when an error is detected.

It is desired to develop a failsafe method and apparatus which handles each processing module of a modular multi-parameter patient monitor separately so that other modules may continue to function when an error is detected in one module. It is also desired that the operator be alerted of unexpected changes of state or of module malfunctions and that the impaired module be placed in a safe state under such error conditions. The present invention has been designed to meet these needs.

SUMMARY OF THE INVENTION

The present invention relates to a failsafe method and apparatus for a parameter module (PM) of a modular multi-parameter patient monitor which meets the above mentioned needs not satisfied by the prior art. The parameter module failsafe system of the invention meets such needs by detecting when the module is malfunctioning and placing such module in a safe state independent of the operation of the other modules. The safe state action will vary depending on the type of module that is malfunctioning.

A preferred embodiment of the multi-parameter modular patient monitor in accordance with the invention monitors the operational state of a module and generates failure signals for placing the module into a safe state when software or hardware errors or other malfunctions are detected. Particularly, the parameter modules of the multi-parameter patient monitor are used to collect parameter data related to the physiological parameters of a patient and to communicate with a patient monitor which displays the collected parameter data. For this purpose, the parameter module collects the required parameter data, processes the parameter data and indicates to the acquisition unit (AU) whether the parameter data has been collected and processed correctly. If so, the processed parameter data is communicated to the patient monitor for display.

During operation, the processing module employs the failsafe method of the invention to check if the module is operating properly. This is accomplished by monitoring the module's software execution sequence and overflowing a watchdog timer to signify an improper execution sequence. In particular, if the watchdog timer overflows as a result of an improper software execution sequence, the module is placed into a "safe state". Also, communications to the acquisition unit are halted, and, in response, the acquisition unit electrically isolates the impaired module while continuing to supply power to other functioning modules.

In accordance with another aspect of the invention, the parameter module's processor may perform a comparison of the acquisition unit processor's time-base and the parameter module's time-base. If the time-bases are out of specification, the parameter module's processor assumes the parameter module's clock is at fault and causes the watchdog timer to overflow so that the module is again placed in a safe state and the parameter module is electrically isolated by the acquisition unit while the other functioning modules continue to receive power.

The "safe state" mode is designed to protect the patient from any hazards that may arise from a malfunctioning parameter module and varies depending on the type of parameter module. For example, to achieve a safe state for a Non-Invasive Blood Pressure (NIBP) module, the pump supplying air to a blood pressure cuff located on the patient's limb is turned off and the cuff's valves are opened to release any trapped air. The NIBP parameter module is then powered down. Comparatively, for an electrocardiogram (ECG) module, the safe state is achieved by turning off the power supply to the ECG parameter module and the ECG signal gathering electrodes.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings of which.

DETAILED DESCRIPTION OF PRESENTLY PREFERRED EMBODIMENTS

A failsafe supervisor system with the above-mentioned beneficial features in accordance with a presently preferred exemplary embodiment of the invention will be described below with reference to FIGS. 1–6. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

The present invention relates to a failsafe supervisor system which provides for the safe operation of a parameter module of a modular multi-parameter patient monitor so as to minimize the likelihood of harm to the patient when a hardware or software error is detected in the parameter module of the patient monitor during operation, and which, when such errors are detected, provides for a consistent and failsafe operation for the parameter modules. As used herein, a "failsafe" system is a system which places the processing module in a state which is non-hazardous to the patient or operator when an invalid state is detected. For example, in the event that an invalid state is detected in the control logic of the parameter module's processor, the "failsafe" system places the module in a known safe state, and no data is processed until the impaired parameter module is returned to normal through a software or hardware reset. A preferred embodiment of a modular multi-parameter patient monitor which implements such a failsafe system in accordance with the invention is illustrated in FIG. 1.

Figure 1:
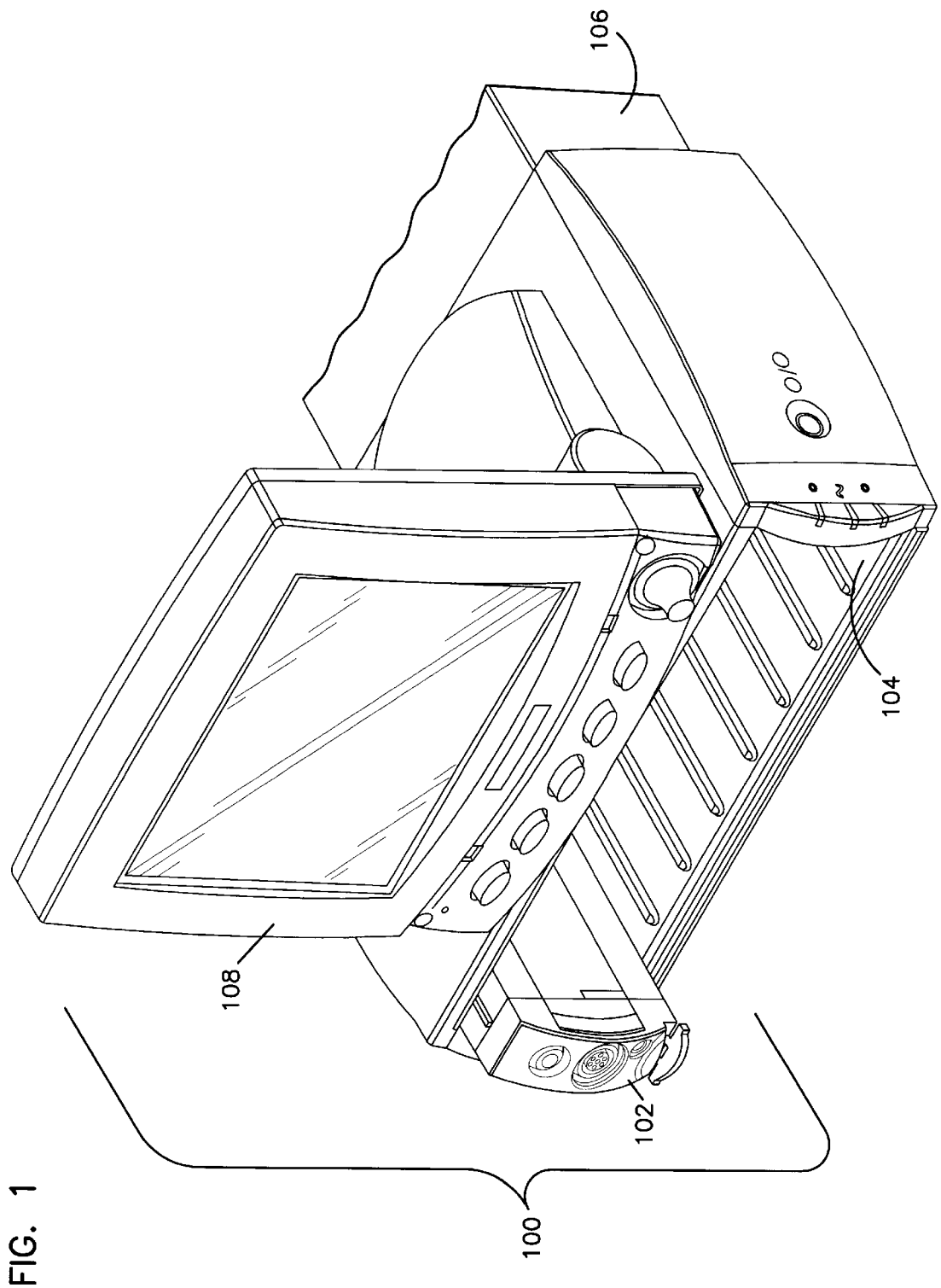
FIG. 1 is a perspective view of a modular patient monitor adapted to accept parameter modules in accordance with the invention.

FIG. 1 is a front perspective view of a modular patient monitor 100, such as the DINAMAP[198] MPS Select Monitor assigned to the present assignee, which accepts parameter modules 102 in docking bay 104 in accordance with a preferred embodiment of the invention. Preferably, docking bay 104 functions as a connection receptacle for a plurality of (e.g., nine) parameter modules 102 and provides inputs to a main housing containing an acquisition unit 106, which includes, among other things, a driver for an articulating display 108. The parameter modules 102 are respective electronic modules which mate with the acquisition unit 106 via the docking bay 104 during use to selectively monitor a patient's vital signs by collecting patient parameter data such as $CO_2$ exhaled by the patient, the patient's heart rate, the patient's blood pressure (invasive or noninvasive), the patient's temperature, the patient's electrocardiogram, the oxygen saturation ($SpO_2$) of the patient's arterial blood, and/or the patient's respiration rate. The parameter modules 102 process data from transducers to generate waveforms and numeric data which are communicated to a processor of the acquisition unit 106 for display on articulating display 108 for use by the clinician in diagnosing the patient's condition.

Figure 2:
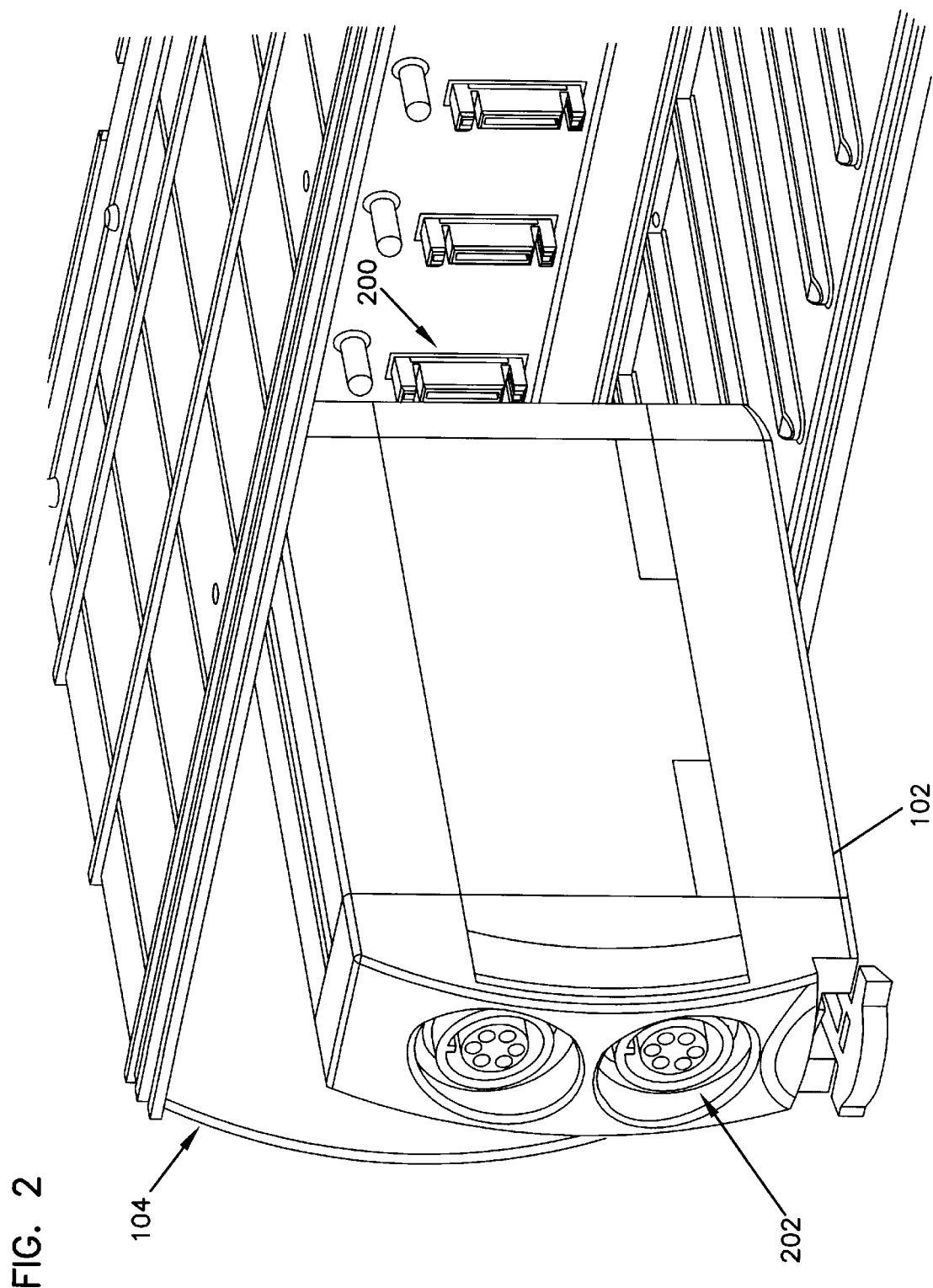
FIG. 2 is an exploded view of the modular patient monitor of FIG. 1 depicting the placement of a parameter module into the patient monitor's housing.

FIG. 2 is an exploded perspective view of the modular patient monitor 100 of FIG. 1. As illustrated, parameter modules 102 are placed in the docking bay 104 and are connected to the acquisition unit 106 via a plurality of patient monitor ports 200. The connection made between the parameter module 102 and the acquisition unit 106 facilitates the communication of parameter data between a processor of a parameter module 102 and a processor of the acquisition unit 106. Ports 202 on the parameter module 102 accept data collection probes applied to the patient for collection of the parameter data.

Figure 3:
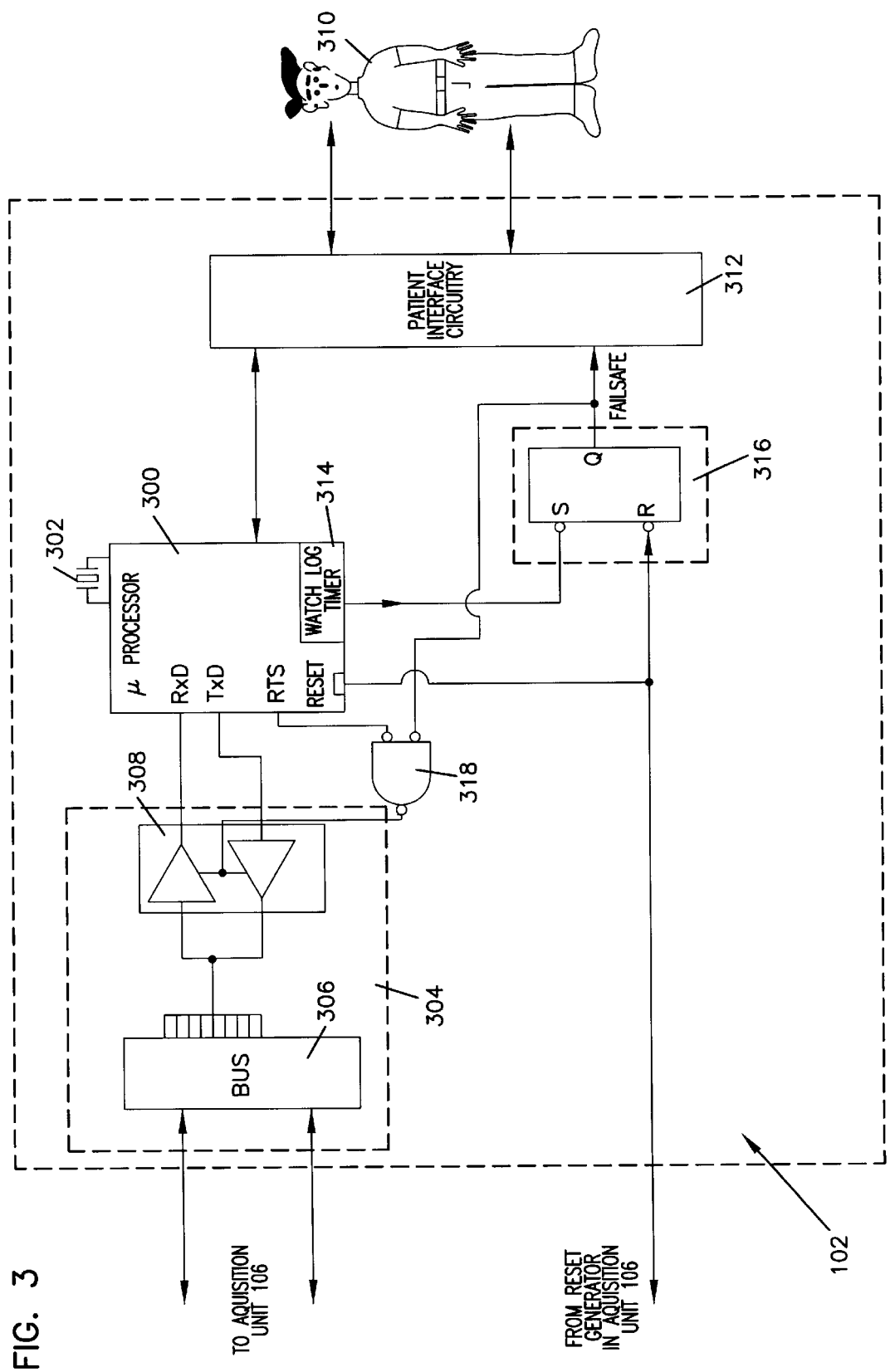
FIG. 3 illustrates a schematic diagram of the hardware implementation of a parameter module including the failsafe apparatus of the invention.

FIG. 3 is a schematic diagram showing the failsafe hardware of the parameter module 102 of the invention. As shown in FIG. 3, the parameter module 102 has a processor 300 driven by a crystal oscillator 302 which communicates with a processor of the acquisition unit 106 of the patient monitor 100 through a communications subsystem 304 including a serial data bus 306 and a data transceiver 308. Processor 300 also receives parameter data from patient 310 via patient interface circuitry 312, which typically includes probes and the like which are connected to ports 202 of the parameter module 102 for the collection of patient parameter data. In a preferred embodiment of the invention, processor 300 is an MC68302 processor which includes an internal watchdog timer 314 which provides an overflow signal to a cross-coupled R-S latch 316 when a malfunction is detected. In turn, R-S latch 316 provides a FAILSAFE signal to the patient interface circuitry 312 to power down such circuitry as needed. As will be explained in more detail below, the FAILSAFE signal preferably further disables the communications subsystem 304 via logic gate 318. As will be appreciated by those skilled in the art, the failsafe operation of a particular module 102 varies in accordance with the type of parameter module 102.

During normal operation, the watchdog timer 314 is set to overflow in a preset time (nominally eight seconds). If the parameter module 102 is operating properly, the watchdog timer 314 is reset by the processor 300 before overflowing. In accordance with the invention, processor 300 determines proper operation by checking whether the hardware is functioning properly as well as whether there is proper execution of the software running on the processor 300. In a preferred embodiment of the invention, the software has several interlocked code sections, one in a high priority task or interrupt service routine, and one in a low priority or background task. The software is designed so that both code sections must run in a prescribed sequence before the watchdog timer 314 is reset. If the code execution sequence is violated, as could be caused by hardware or software failure, the watchdog timer 314 is not reset by the processor 300 and provides an overflow output which sets the R-S latch 316. The R-S latch 316 changes state setting the FAILSAFE signal to TRUE. The FAILSAFE signal then disables the communications subsystem 304 via gate 318 so that the malfunctioning parameter module 102 stops communicating with the acquisition unit 106. In addition, the FAILSAFE signal causes the patient interface circuitry 312 to enter a known safe state by turning off all potentially hazardous devices such as pumps, valves, isolated power supplies, and the like. For example, to achieve a safe state for a Non-Invasive Blood Pressure (NIBP) module, the pump supplying air to a blood pressure cuff located on the patient's limb is turned off and the cuff's valves are opened to release any trapped air. The NIBP parameter module is then powered down. On the other hand, for an electrocardiogram (ECG) parameter module, the safe state is achieved by disabling the isolated power supply to the ECG parameter module and the ECG signal gathering electrodes.

The R/S latch 316 remains in a safe (SET) state until either a hardware reset is provided from a reset generator of the acquisition unit 106 or a power cycle reset is provided from the processor 300. Preferably, processor 300 ceases to transmit and receive data to/from the acquisition unit 106 through the communications subsystem 304 so long as the safe state is asserted, thereby preventing potentially contaminated data from being provided to the acquisition unit 106 for display on display 108.

The failsafe method of the invention, as implemented by the processor 300, will now be described with respect to the flow chart of FIG. 4.

Figure 4:
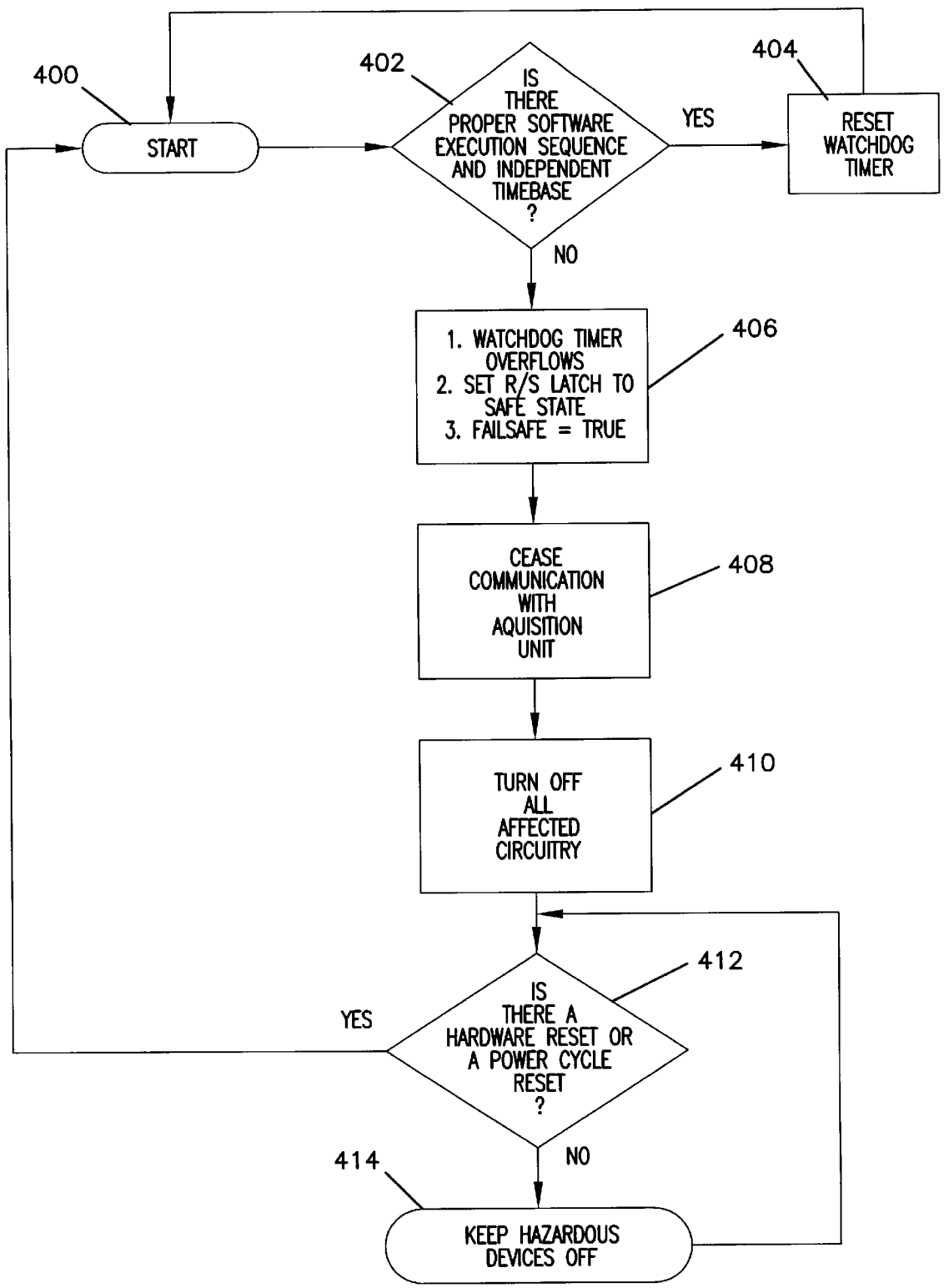
FIG. 4 illustrates a flow diagram of the failsafe method of the invention implemented on the parameter module of FIG. 3.

FIG. 4 illustrates a flow diagram of the failsafe technique of the invention as implemented in software on the processor 300 of the parameter module 102. As illustrated, the failsafe method starts at step 400 where processor determines at step 402 whether the software is executing in the correct sequence and checks the independent time base to verify that the module processor 300 is synchronized with the processor of the acquisition unit 106. In a preferred embodiment, this latter feat is accomplished by having the module processor 300 sum up the number of system polling packets received by the module processor 300 via the serial data bus 306 over a predetermined time period (e.g., 10 seconds). The module processor 300 compares the sum to the expected value (e.g., 100 packets would be expected in 10 seconds if 10 packets /second are expected) plus or minus a tolerance. The tolerance number is specific to each parameter module based on its parameters and the accuracy required and is stored in the program memory of the parameter module 102. Preferably, if the module processor 300 detects an out of specification, the module processor 300 assumes the clock of the parameter module 102 is at fault and sends an error message to the acquisition unit before entering the "fatal" state by setting the FAILSAFE signal to "TRUE" at step 406.

Such time-base checking is particularly desirable in accordance with the invention because synchronizing the parameter module's processor 300 with the acquisition unit's processor permits time-slotted synchronous communications which, in turn, allows the parameter data from a plurality of parameter modules 102 to be communicated to the acquisition unit's processor without the use of interrupts. Accordingly, it is desirable in accordance with the invention to keep the processors synchronized to permit such synchronous communications and to take a parameter module 102 off-line when its clock is out of specification.

In addition, those skilled in the art will appreciate that an independent time base is required to verify the accuracy of a derived heart rate parameter in a multi-parameter patient monitor. A secondary reason is to ensure that the cuff inflation time does not exceed regulatory specification.

If the software execution sequence is proper and the time base is within tolerance, the watchdog timer 314 of the processor 300 is reset at step 404 and the hardware/software check sequence is repeated. However, if an error is detected in the software execution sequence, the time base is out of specification, or some other hardware or software error is detected, the watchdog timer 314 is not reset and hence overflows at step 406. The overflow of the watchdog timer 314 causes the R-S latch 316 to set FAILSAFE=TRUE, thereby causing the patient interface circuitry 312 to be placed in a known safe state and the FAILSAFE signal to disable the communication subsystem 304. Once the safe state is asserted, processor 300 ceases communication with the acquisition unit 106 at step 408. All circuitry which may be affected by the error is powered down at step 410. For example, the associated patient interface circuitry 312 as well as the parameter module 102 are powered down to a known safe state. Once powered down, a hardware reset from a reset generator of the acquisition unit 106 or a power cycle reset (initiation of power to the processor 300) may reset the R-S latch 316 at step 412 for a resumption of normal operation once the error has been isolated and corrected. Otherwise, the parameter module 102 and the associated patient interface circuitry 312 are kept powered down at step 414.

Figure 5:
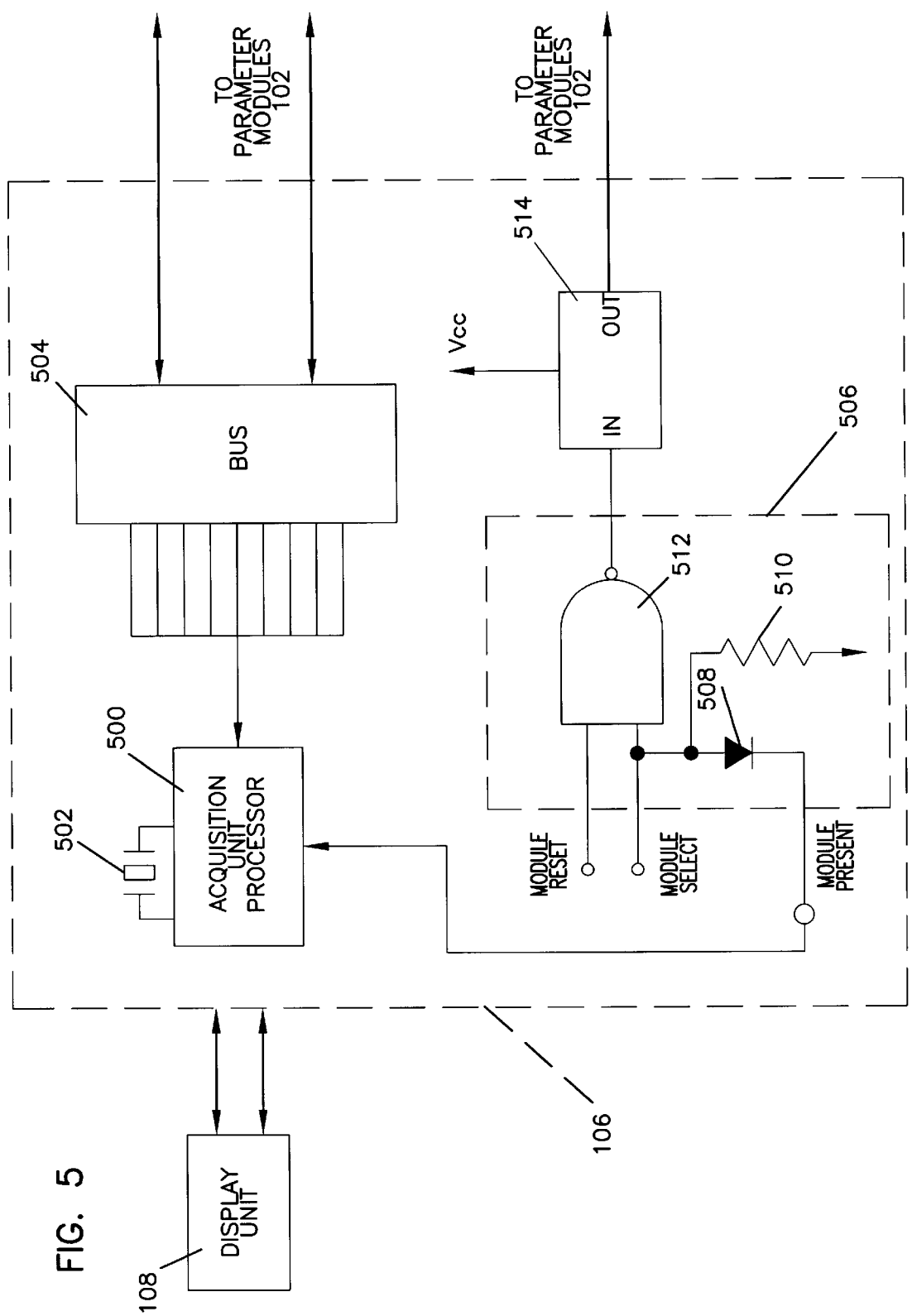
FIG. 5 illustrates a schematic diagram of the hardware implementation of an acquisition unit including the failsafe apparatus of the invention.

FIG. 5 is a schematic diagram of the hardware implementation of the failsafe portion of the acquisition unit 106. Processor 500 of the acquisition unit 106 is driven by a crystal oscillator 502 and communicates with the parameter module's processor 300 through a serial data bus 504. Processor 500 receives patient parameter information from the module processor 300 of each connected parameter module 102 and presents the parameter data to articulating display 108 for evaluation by the clinician. When a parameter module 102 ceases to communicate with the acquisition unit 106, processor 500 determines whether that particular parameter module 102 is still connected to the acquisition unit 106 via connector 200 (FIG. 2). A simple module detection circuit 506 is provided for this purpose. As shown, the module detection circuit 506 includes a diode 508, a pull up resistor 510, and a logical NAND gate 512. The presence of the parameter module 102 pulls low the module select line of the NAND gate 512 which is otherwise held high by pull up resistor 510 in the absence of a parameter module 102. A module reset input line of the NAND gate 512 allows a reset pulse to be generated by reset pulse generator 514 when the parameter module 102 is present and a module reset pulse is provided. In particular, when the parameter module 102 is present and a "Module Reset" pulse is provided, NAND gate 512 outputs a pulse to a reset generator 514 which, in turn, provides a reset signal to the R-S latch of the parameter module 102 to cause the parameter module to be placed in a safe state. If the parameter module 102 is determined to be present but not communicating with the processor 500, then it is determined by processor 500 that the parameter module 102 is malfunctioning, and the processor 500 further electrically isolates the parameter module 102. The parameter module 102 is kept electrically isolated until the error is corrected and the parameter module's R-S latch is once again "set."

The failsafe method of the invention, as implemented by the processor 500, will now be described with respect to the flow chart of FIG. 6.

Figure 6:
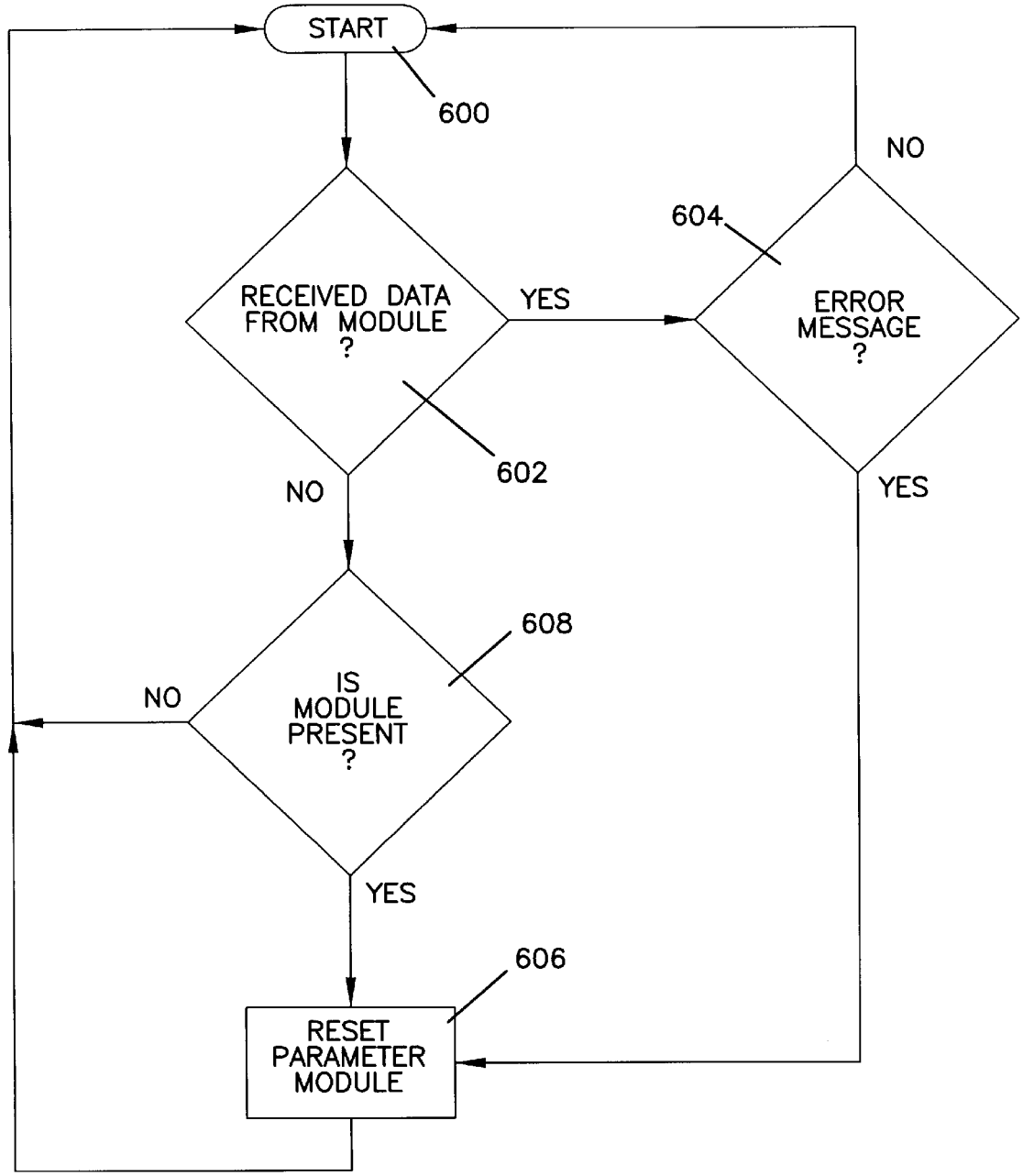
FIG. 6 illustrates a flow diagram of the failsafe method of the invention implemented on the acquisition unit of FIG. 5.

FIG. 6 illustrates a flow diagram of the failsafe method of the invention implemented on the acquisition unit's processor 500 of FIG. 5. As illustrated in FIG. 6, the failsafe method starts at step 600 where the processor 500 first polls the parameter module 102 to determine if any parameter data is available from a parameter module 102 via serial data bus 504 at step 602. If parameter data is received, the processor 500 checks at step 604 whether the message received from the parameter module 102 is an error message. If the message is not an error message, control returns to step 600 and steps 602 and 604 are repeated. However, if the message is an error message, then the parameter module 102 is reset via hardware at step 606, while power to other parameter modules is maintained. An appropriate error message is also preferably displayed on the articulating display 108.

On the other hand, if no data is received in response to the polling by the processor 500 at step 602, processor 500 checks at step 608 to determine if a parameter module 102 is present. If not, then control returns to step 600 and the process is repeated. However, if a module is present and no data was received, this is likely because the parameter module 102 has detected an error and disabled the communication subsystem 304 (FIG. 3). Accordingly, if the parameter module 102 is determined to be present at step 608, then processor 500 performs a hardware reset at step 606 but does not re-establish communications with the parameter module 102. This causes the parameter module 102 to place the patient interface circuitry 312 into a known safe state, because on reset the system is designed to turn off all potentially hazardous devices such as pumps, valves, isolated power supplies, and the like. The parameter module 102 remains electrically isolated at step 606 until a module reset signal is received. Control returns to step 600 and the process is repeated.

Although an exemplary embodiment of the invention has been described in detail above, those skilled in the art will readily appreciate that many additional modifications are possible in the exemplary embodiment without materially departing from the novel teachings and advantages of the invention. For example, those skilled in the art will appreciate that the acquisition unit's processor of the present invention must query the parameter module often enough to be able to safely detect that the parameter module is no longer responding and to assume a safe state if this occurs. In the description above, it was assumed that the appropriate signals and/or logic connections would reset the R-S latch of the parameter module; however, the same results may be achieved by simply removing power from the parameter module. Accordingly, all such modifications are intended to be included within the scope of this invention as defined in the following claims.

What is claimed is:

1. A failsafe system for a multi-parameter patient monitor which collects parameter data related to physiological parameters of a patient via patient interface circuitry and displays said parameter data on a display, said failsafe system comprising:

a watchdog timer which is reset within a predetermined period of time so long as said patient monitor is operating properly;

a failsafe signal generator responsive to an overflow output of said watchdog timer, said failsafe signal generator generating a failsafe signal which places said patient interface circuitry in a safe state when said watchdog timer provides an overflow signal to an input thereof; and a disable circuit which disables the output of parameter data to said display upon receipt of said failsafe signal.

2. A failsafe system as in claim 1, wherein said patient monitor includes a parameter processing module having a module processor which checks an execution sequence of software loaded thereon and resets said watchdog timer within said predetermined period of time so long as said execution sequence is correct.

3. A failsafe system as in claim 2, wherein said patient monitor includes an acquisition unit having a display processor which presents parameter data to said display, wherein said module processor compares a time base of said display processor to a time base of said module processor and resets said watchdog timer within said predetermined period of time so long as said time bases compare within a predetermined tolerance.

4. A failsafe system as in claim 3, wherein said failsafe signal generator is a Reset-Set latch which receives said overflow signal from said watchdog timer at a set input and outputs said failsafe signal upon receipt of a reset signal from said display processor or said module processor.

5. A failsafe system as in claim 4, wherein said display processor provides said reset signal to said Reset-Set latch when said display processor detects that said parameter processing module is connected to said acquisition unit but not transmitting parameter data for display.

6. A failsafe system as in claim 1, wherein said disable circuit includes a data transceiver and a logic gate which disables said transceiver upon receipt of said failsafe signal.

7. A modular multi-parameter patient monitor which collects parameter data related to physiological parameters of a patient, comprising:

a display;

patient interface circuitry which collects said parameter data from said patient;

a parameter module responsive to parameter data from said patient interface circuitry, said parameter module including a module processor which processes said parameter data and a data output circuit which outputs processed parameter data;

an acquisition unit which receives said processed parameter data from said parameter module and presents said processed parameter data to said display; and a failsafe system comprising a watchdog timer which is reset within a predetermined period of time so long as said parameter module is operating properly and a failsafe signal generator responsive to an overflow output of said watchdog timer, said failsafe signal generator generating a failsafe signal which disables said data output circuit and places said patient interface circuitry and parameter module in a safe state when said watchdog timer provides an overflow signal to an input thereof.

8. A patient monitor as in claim 7, wherein said module processor checks an execution sequence of software loaded thereon and resets said watchdog timer within said predetermined period of time so long as said execution sequence is correct.

9. A patient monitor as in claim 8, wherein said acquisition unit comprises a display processor which presents parameter data from said parameter module to said display, and said module processor compares a time base of said display processor to a time base of said module processor and resets said watchdog timer within said predetermined period of time so long as said time bases compare within a predetermined tolerance.

10. A patient monitor as in claim 9, wherein said failsafe signal generator is a Reset-Set latch which receives said overflow signal from said watchdog timer at a set input and outputs said failsafe signal upon receipt of a reset signal from said display processor or said module processor.

11. A patient monitor as in claim 10, wherein said acquisition unit comprises a detection circuit which detects a connection of said parameter module to said acquisition unit, said display processor providing said reset signal to said Reset-Set latch when said detection circuit detects the connection of said parameter module to said acquisition unit but said display processor does not receive parameter data from said parameter module for display.

12. A patient monitor as in claim 7, wherein said data output circuit includes a data transceiver and said failsafe system includes a logic gate which disables said transceiver upon receipt of said failsafe signal.

13. A patient monitor as in claim 7, further comprising a plurality of parameter modules which provide parameter data to said acquisition unit for display, whereby said failsafe system generates separate failsafe signals for each parameter module and whereby each parameter module for which a failsafe signal is generated and its associated patient interface circuitry is placed in said safe state while other parameter modules continue normal operation.

14. A failsafe method for a multi-parameter patient monitor which collects parameter data related to physiological parameters of a patient via patient interface circuitry and displays said parameter data on a display, said failsafe method comprising the steps of:

checking an execution sequence of software of said patient monitor and resetting a watchdog timer within a predetermined period of time so long as said execution sequence is correct;

generating a failsafe signal in response to an overflow output from said watchdog timer, said failsafe signal placing said patient interface circuitry in a safe state; and disabling the output of parameter data to said display upon receipt of said failsafe signal.

15. A failsafe method for a modular multi-parameter patient monitor comprising an acquisition unit and at least one parameter module which collects parameter data related to physiological parameters of a patient via patient interface circuitry and provides said parameter to said acquisition unit for display of said parameter data on a display, said failsafe method comprising the steps of:

comparing a time base of a display processor of said acquisition unit to a time base of a module processor of said at least one parameter module and resetting a watchdog timer of said at least one parameter module within a predetermined period of time so long as said time bases compare within a predetermined tolerance;

generating a failsafe signal in response to an overflow output from said watchdog timer, said failsafe signal placing said patient interface circuitry in a safe state; and disabling the output of parameter data to said display upon receipt of said failsafe signal.

16. A method as in claim 15, wherein said patient monitor comprises at least two parameter modules, comprising the steps of generating separate failsafe signals for each parameter module and placing a parameter module for which a failsafe signal has been generated and its associated patient interface circuitry in said safe state while any other parameter modules continue normal operation.

17. A method as in claim 15, comprising the further steps of determining whether said at least one parameter processing module is connected to said acquisition unit but not transmitting parameter data and causing said failsafe signal to be generated in said generating step when said at least one parameter processing module is connected to said acquisition unit but not transmitting data.

* * * * *